United States Patent [19]

Khalaf

[11] Patent Number: 6,042,824
[45] Date of Patent: *Mar. 28, 2000

[54] METHODS USING CROSS LINKED PROTEIN CRYSTAL FORMULATIONS AS CATALYSTS IN ORGANIC SOLVENTS

[75] Inventor: Nazer K. Khalaf, Worcester, Mass.

[73] Assignee: Altus Biologics, Inc., Cambridge, Mass.

[ * ] Notice: This patent is subject to a terminal disclaimer.

[21] Appl. No.: 08/868,088

[22] Filed: Jun. 3, 1997

Related U.S. Application Data

[62] Division of application No. 08/652,964, May 24, 1996, Pat. No. 5,932,212.

[51] Int. Cl.$^7$ .............................. A61K 38/43; C12N 9/00
[52] U.S. Cl. ...................... 424/94.6; 424/94.5; 424/94.3; 424/94.2; 435/183; 435/188; 435/188.5; 435/195; 514/4; 514/2
[58] Field of Search ................................ 435/195, 188.5, 435/188, 184, 183; 424/94.6, 94.5, 94.3, 94.2; 514/4, 2

[56] References Cited

U.S. PATENT DOCUMENTS

| | | | |
|---|---|---|---|
| 4,267,234 | 5/1981 | Rembaum | 428/403 |
| 4,369,226 | 1/1983 | Rembaum | 428/334 |
| 5,152,903 | 10/1992 | Neff et al. | 210/734 |

FOREIGN PATENT DOCUMENTS

| | | | |
|---|---|---|---|
| WO 4344211A | 6/1995 | Germany | C12N 9/96 |
| WO 92/02617 | 2/1992 | WIPO | C12N 11/00 |
| WO 94/25560 | 11/1994 | WIPO | C11D 11/00 |
| WO 94/28118 | 12/1994 | WIPO | C12N 11/00 |
| WO 95/15371 | 6/1995 | WIPO | C11D 3/386 |
| WO 95/17504 | 6/1995 | WIPO | C12N 9/20 |

OTHER PUBLICATIONS

A.D. Blackwood et al., "Organic Phase Buffers' Control Biocatalyst Activity Independent of Initial Aqueous pH", *Biochim. Biophys. Acta*, 1206, pp. 161–165 (1994).
S. Bornemann et al., "The Effects of Surfactants on Lipase–Catalysed Hydrolysis of Esters: Activities and Stereoselectivity", *Biocatalysis*, 11, pp. 191–221 (1994).
R. Bovara et al., "Resolution of (±)–trans–Sobrerol by Lipase PS–Catalyzed Transesterification and Effects of Organic Solvents on Enantioselectivity", *Tetrahedron: Asymmetry*, 2, pp. 931–938 (1991).
R. Bovara et al., "Water Activity does not Influence the Enantioselectivity of Lipase PS and Lipoprotein Lipase in Organic Solvents", *Biotechnol. Lett.*, 15, pp. 169–174 (1993).
K. Dabulis and A.M. Kilbanov, "Dramatic Enhancement of Enzymatic Activity in Organic Solvents by Lyoprotectants", *Biotechnol. Bioeng.*, 41, pp. 566–571 (1993).
K. Faber and M.C.R. Franssen, "Prospects for the Increased Application of Biocatalysts in Organic Transformations", *Trends in Biochem. Tech.*, 11, pp. 461–470 (1993).

M. Goto et al., "Design of Surfactants Suitable for Surfactant–Coated Enzymes as Catalysts in Organic Media", *J. Chem. Eng. Jpn.*, 26, pp. 109–111 (1993).
V. Gotor et al., "Enzymatic Aminolysis and Transamidation Reactions", *Tetrahedron*, 47, pp. 9207–9214 (1991).
J.M. Guisán et al., "Insolubilized Enzyme Derivatives in Organic Solvents: Mechanisms of Inactivation and Strategies for Reactivation", *Biocatalysis*, pp. 221–228 (1992).
A. Kabanov et al., "Regulation of the Catalytic Activity and Oligomeric Composition of Enzymes in Reversed Micelles of Surfactants in Organic Solvents", *FEBS*, 278, pp. 143–146 (1991).
N. Kamiya et al., "Surfactant–Coated Lipase Suitable for the Enzymatic Resolution of Methanol as a Biocatalyst in Organic Media", *Biotechnol. Prog.*, 11, pp. 270–275 (1995).
Y.L. Khmelinitsky et al., "Salts Dramatically Enhance Activity of Enzymes Suspended in Organic Solvents", *J. Am. Chem. Soc.*, 116, pp. 2647–2648 (1994).
A.M. Kilbanov, "Immobilized Enzymes and Cells as Practical Catalysts", *Science*, 219, pp. 722–727 (1983).
A. M. Kilbanov, "Enzymatic Catalysis in Anhydrous Organic Solvents", *Trends in Biochem. Sci.*, 14, pp. 141–144 (1989).
A.M. Kilbanov, "Asymmetric Transformations Catalyzed by Enzymes in Organic Solvents", *Acc. Chem. Res.*, 23, pp. 114–120 (1990).
J.J. Lalonde et al., "Cross–Linked Crystals of *Candida rugosa* Lipase: Highly Efficient Catalysts for the Resolution of Chiral Esters", *J. Am. Chem. Soc.*, 117, pp. 6845–6852 (1995).
K.M. Lee et al., "Crosslinked Crystalline Horse Liver Alcohol Dehydrogenase As a Redox Catalyst: Activity and Stability Toward Organic Solvent", *Bioorganic Chem.*, 14, pp. 202–210 (1986).
T. Nishio et al., "Ester Synthesis in Various Organic Solvents by Three Kinds of Lipase Preparations Derived from *Pseudomonas fragi* 22.39B", *Agric. Biol. Chem.*, 52, pp. 2631–2632 (1988).
B. Nordvi et al., "Effect of Polyhydroxy Compounds on the activity of Lipase from *Rhizopus arrhizus* in Organic Solvent", *Biocatalysis in Non–Conventional Media*, J. Tramper et al. (Ed.), pp. 355–361 (1992).
Y. Okahata et al., "A Lipid–Coated Lipase as an Enantioselective Ester Synthesis Catalyst in Homogeneous Organic Solvents", *J. Org. Chem.*, 60, pp. 2244–2250 (1995).

(List continued on next page.)

*Primary Examiner*—Keith D. MacMillan
*Assistant Examiner*—T. D. Wessendorf
*Attorney, Agent, or Firm*—Fish & Neave; James F. Haley, Jr.; Margaret A. Pierri

[57] ABSTRACT

The present invention relates to the application of biocatalysis technology for performing selective chemical reactions. In one embodiment, this invention relates to crosslinked protein crystal formulations and their use as catalysts in chemical reactions involving organic solvents. This invention also provides methods for producing crosslinked protein crystal formulations and methods using them to optimize chemical reactions in organic solvents, including those used in industrial scale chemical processes.

9 Claims, No Drawings

OTHER PUBLICATIONS

G. Ottolina et al., "Effect of the Enzyme Form on the Activity, Stability and Enantioselectivity of Lipoprotein Lipase in Toluene", *Biotechnol. Lett.,* 14, pp. 947–952 (1992).

A. Palomer et al., "Resolution of rac–Ketoprofen Esters by Enzymatic Reactions in Organic Media", *Chirality,* 5, pp. 320–328 (1993).

V.M. Paradkar and J.S. Dordick, "Aqueous–like Activity of α–Chymotrypsin Dissolved in Nearly Anhydrous Organic Solvents", *J. Am. Chem. Soc.,* 116, pp. 5009–5010 (1994).

R.A. Persichetti et al., "Cross–Linked Enzyme Crystals (CLECs) of Thermolysin in the Synthesis of Peptides", *J. Am. Chem., Soc.,* 117, pp. 2732–2737 (1995).

I. Skúladóttir et al., "Cryo–bioorganic Synthesis—Enzyme Catalysis at Low Temperature and in Low Water Content Environments", *Biocatalysis in Non–Conventional Media,* J. Tramper et al. (Ed.), pp. 307–312 (1992).

N.L. St. Clair et al., "Cross–linked Enzyme Crystals as Robust Biocatalysts", *J. Am. Chem. Soc.,* 114, pp. 7314–7316 (1992).

Y.–F. Wang et al., "Lipase–Catalyzed Irreversible Transesterifications Using Enol Esters as Acylating Reagents: Preparative Enantio– and Regioselective Syntheses of Alcohols, Glycerol Derivatives, Sugars, and Organometallics", *J. Am. Chem. Soc.,* 110, pp. 7200–7205 (1988).

E. Wehtje et al., "Stabilization of Adsorbed Enzymes Used as Biocatalysts in Organic Solvents", *Biocatalysis in Non–Conventional Media,* J. Tramper et al. (Ed.), pp. 377–382 (1992).

E. Wehtje et al., "Improved Activity Retention of Enzymes Deposited on Solid Supports", *Biotechnol. Bioeng.,* 41, pp. 171–178 (1993).

T. Yamane et al., "Intramolecular Esterification by Lipase Powder in Microaqueous Benzene: Factors Affecting Acitivity of Pure Enzyme", *Biotechnol. Bioeng.,* 36, pp. 1063–1069 (1990).

N. Khalaf et al., "Cross–Linked Enzyme Crystals as High Active Catalysts in Organic Solvents", *J. Am. Chem. Soc.,* 118, pp. 5494–5495 (1996).

Y.F. Wang et al., "Cross–Linked Crystals of Subtilisin; Versatile Catalysts for Organic Synthesis", *Ann. N.Y. Acad. Sci.,* 799, pp. 777–783 (1996).

6,042,824

METHODS USING CROSS LINKED PROTEIN CRYSTAL FORMULATIONS AS CATALYSTS IN ORGANIC SOLVENTS

This is a division of application Ser. No. 08/652,964, filed May 24, 1996, now U.S. Pat. No. 5,932,212 entitled Crosslinked Protein Crystal Formulations and Their Use as Catalysts in Organic Solvents.

TECHNICAL FIELD OF THE INVENTION

The present invention relates to the application of biocatalysis technology for performing selected chemical reactions. In one embodiment, this invention relates to crosslinked protein crystal formulations and their use as catalysts in chemical reactions involving organic solvents. This invention also provides methods for producing crosslinked protein crystal formulations and methods using them to optimize chemical reactions in organic solvents, including those used in industrial scale chemical processes.

BACKGROUND OF THE INVENTION

The use of proteins, such as enzymes, as catalysts in industrial-scale synthesis of specialty chemicals and pharmaceuticals has received much attention in recent years [K. Faber and M. C. R. Franssen, *Trends in Biochem. Tech.*, 11, pp. 461–70 (1993)]. Enzymes are recognized as useful tools for accomplishing chemical reactions in a stereo-, regio- and chemoselective manner. The ability of enzymes to function under mild conditions, ease of disposal and minimal waste production are further advantages associated with their use. Enzymes are also used for catalysis in organic solvents to solubilize substrates and products and to manipulate reaction kinetics and equilibrium in order to increase product yield.

While enzymes offer impressive synthetic potential over current nonenzymatic technology, their commercial use has been limited by disadvantages such as poor stability, variability in performance, difficulty of isolation and purification, difficulty in handling, high cost and long reaction times. Furthermore, organic solvents are often incompatible with enzymes, leading to enzyme degradation or inactivation [A. M. Klibanov, "Asymmetric transformations Catalyzed by Enzymes in Organic Solvents", *Acc. Chem. Res.*, 23, pp. 114–20 (1990]. In order for enzymes to function as viable industrial catalysts, they must be able to function without excessive intervention in the practical environments of manufacturing processes. Such environments include polar and non-polar organic solvents and aqueous-organic solvent mixtures. The low activity of enzymes and their aversion to organic solvents have remained barriers to widespread use of these proteins in routine organic syntheses. Even when such syntheses are catalyzed by enzymes, it is not unusual to see processes employing more enzyme than substrate by weight. See, for example, R. Bovara et al., *Tetrahedron: Asymmetry*, 2, pp. 931–38 (1991); Y. -F. Wang et al., *J. Am. Chem. Soc.*, 110, pp. 7200–05 (1988); A. Palomaer et al., *Chirality*, 5, pp. 320–28 (1993) and V. Gotor et al., *Tetrahedron*, 47, pp. 9207–14 (1991).

Two methods designed to overcome these disadvantages—enzyme purification and enzyme immobilization—have addressed some of these disadvantages. However, they have not solved the problem of loss of enzyme activity or stability in organic solvents. Immobilization has actually exacerbated these problems by incurring higher costs and diluting the activity of the enzyme by the addition of support materials. Enzyme purification also incurs added cost and, in most cases fails to increase enzyme activity in organic solvents. For example, the potential synthetic benefits of purified lipases in organic solvents have not been realized [T. Nishio and M. Kamimura, *Agric. Biol, Chem.*, 52, pp. 2631–32 (1988); T. Yamane et al., *Biotechnol. Bioeng.*, 36, pp. 1063–69 (1990)]. The cost of purified lipases is higher than that of their crude counterparts, while their stability and activity in organic solvents is lower [R. Bovara et al., *Biotechnol. Lett.*, 15, pp. 169–74 (1993); E. Wehtje et al., *Biotechnol. Bioeng.*, 41, pp. 171–78 (1993); G. Ottolina et al., *Biotechnol. Lett.*, 14, pp. 947–52 (1992)].

Recent studies have demonstrated that enzyme activity in organic solvents is intimately related to water content, size and morphology of the catalyst particles and the enzyme microenvironment [A. M. Klibanov, "Enzymatic Catalysis in Anhydrous Organic Solvents", *Trends in Biochem. Sci.*, 14, pp. 141–44 (1989)]. These parameters have been adjusted by preparing lyophilized complexes of enzymes with carbohydrates, organic buffers or salts [K. Dabulis and A. M. Klibanov, *Biotechnol. Bioeng.*, 41, pp. 566–71 (1993); A. D. Blackwood et al., *Biochim. Biophys. Acta*, 1206, pp. 161–65 (1994); Y. L. Khmelnitsky et al., *J. Am. Chem. Soc.*, 116, pp. 2647–48 (1994)]. However, despite the widespread use of lyophilization for preparation of enzymes for catalysis in organic solvents, its impact is not fully understood and, in some instances, it may cause significant reversible denaturation of enzymes [Dabulis and Klibanov, supra].

Other approaches to the problem of low enzyme activity in biotransformations involving organic solvents have included the use of surfactants. It has been reported that non-ionic surfactants added prior to immobilization of lipase into a photo-crosslinkable resin pre-polymer, or added to the reaction incubation mixture, increase enzyme activity [B. Nordvi and H. Holmsen, "Effect of Polyhydroxy Compounds on the activity of Lipase from *Rhizopus arrhizus* in Organic Solvent", in *Biocatalysis in Non-Conventional Media*, J. Tramper et al. (Ed.), pp. 355–61 (1992)]. Immobilized lipase enzymes prepared by application of a non-ionic surfactant (containing at least one fatty acid moiety) to a hydrophobic support prior to or simultaneously with application of the lipase enzyme demonstrate activity in enzymatic conversion processes comparable with conventional immobilized enzymes [PCT patent application WO 94/28118].

Surfactants have been said to reduce enzymatic activity of lipases [S. Bornemann et al., "The Effects of Surfactants on Lipase-Catalysed Hydrolysis of Esters: Activities and Stereo Selectivity", *Biocatalysis*, 11, pp. 191–221 (1994)]. Nevertheless, surfactants have been mixed with an aqueous solution of an enzyme, the mixture dewatered and the resulting enzyme preparation used as a catalyst said to have enhanced activity in organic solvents [PCT patent application WO 95/17504]. Surfactants or lipids have also been used to coat enzymes in order to solubilize them in organic solvents and, thus, increase chemical reaction rates [M. Goto et al., "Design of Surfactants Suitable for Surfactant-Coated Enzymes as Catalysts in Organic Media", *J. Chem. Eng. Jpn.*, 26, pp. 109–11 (1993); N. Kamiya et al., "Surfactant-Coated Lipase Suitable for the Enzymatic Resolution of Methanol as a Biocatalyst in Organic Media", *Biotechnol, Prog.*, 11, pp. 270–75 (1995)]. After this procedure, the enzymes become soluble in organic solvents. Enzyme complexes soluble in organics are also described in V. M. Paradkar and J. S. Dordick, *J. Am. Chem. Soc.*, 116, pp. 5009–10 (1994) (proteases) and Y. Okahata et al., *J. Org. Chem.*, 60, pp. 2240–50 (1995)(lipases).

The advent of crosslinked enzyme crystal ("CLEC™") technology provided a unique approach to solving the above-described disadvantages [N. L. St. Clair and M. A. Navia, *J. Am. Chem. Soc.*, 114, pp. 7314–16 (1992)]. Crosslinked enzyme crystals retain their activity in environments that are normally incompatible with enzyme (soluble or immobilized) function. Such environments include prolonged exposure to high temperature and extreme pH. Additionally, in organic solvents and aqueous-organic solvent mixtures, crosslinked enzyme crystals exhibit both stability and activity far beyond that of their soluble or conventionally-immobilized counterparts. Since so many biocatalysis processes depend on stability and activity of an enzyme under sub-optimal conditions, crosslinked enzyme crystals are advantageously used in industrial, clinical and research settings enzymes. Thus, crosslinked enzyme crystals represent an important advance in the area of biocatalysis, as attractive and broadly applicable catalysts for organic synthesis reactions [R. A. Persichetti et al., "Cross-Linked Enzyme Crystals (CLECs) of Thermolysin in the Synthesis of Peptides", *J. Am. Chem. Soc.*, 117, pp. 2732–37 (1995) and J. J. Lalonde et al., *J. Am. Chem. Soc.*, 1117, pp. 6845–52 (1995)].

Despite the progress of protein catalysis technology in general, the need still exists for catalysts which have high activity in organic solvents.

DISCLOSURE OF THE INVENTION

The present invention provides crosslinked protein crystal formulations which exhibit high activity and productivity as catalysts in chemical reactions involving organic solvents or aqueous-organic solvent mixtures. Advantageously, this level of activity and productivity is greater than that of soluble or conventionally-immobilized proteins. This invention also provides methods for producing crosslinked protein crystal formulations and methods using them to optimize chemical reactions in organic solvents, including those used in industrial scale biocatalysis.

According to one embodiment of this invention, crosslinked protein crystal formulations are produced by drying crosslinked protein crystals in the presence of a surfactant and an organic solvent. In a second embodiment of this invention, crosslinked protein crystal formulations are produced by lyophilizing crosslinked protein crystals in the presence of a surfactant and an organic solvent.

DETAILED DESCRIPTION OF THE INVENTION

In order that the invention herein described may be more fully understood, the following detailed description is set forth. In the description, the following terms are employed:

Organic Solvent—any solvent of non-aqueous origin.

Aqueous-Organic Solvent Mixture—a mixture comprising n % organic solvent, where n is between 1 and 99 and m % aqueous, where m is 100–n.

Mixture Of Organic Solvents—a combination of at least two different organic solvents in any proportion.

Crosslinked Protein Crystal Formulation—a mixture of crosslinked protein crystals with one ou more additional excipients, such as surfactants, salts, buffers, carbohydrates or polymers, in a dried, free-flowing powder or lyophilized form, rather than a slurry.

Catalytically Effective Amount—an amount of a crosslinked protein crystal formulation of this invention which is effective to protect, repair, or detoxify the area to which it is applied over some period of time.

Reactive Topical Composition—a composition which is effective to protect, repair or detoxify the area to which it is applied over some period of time.

The crosslinked protein crystal formulations of this invention are particularly advantageous because they retain high activity in harsh solvent environments that are typical of many industrial-scale chemical synthesis procedures. As a result of their crystalline nature, the crosslinked protein crystal components of these formulations achieve uniformity across the entire crosslinked crystal volume. This uniformity is maintained by the intermolecular contacts and chemical crosslinks between the protein molecules constituting the crystal lattice, even when exchanged in organic or mixed aqueous-organic solvents. Even in such solvents, the protein molecules maintain a uniform distance from each other, forming well-defined stable pores within the crosslinked protein crystal formulations that facilitate access of substrate to the catalyst, as well as removal of product. In these crosslinked protein crystals, the lattice interactions, when fixed by chemical crosslinks, are particularly important in preventing denaturation, especially in organic solvents or mixed aqueous-organic solvents. Crosslinked protein crystals and the constituent proteins within the crystal lattice remain monodisperse in organic solvents, thus avoiding the problem of aggregation. These features of the crosslinked protein crystal components of crosslinked protein crystal formulations of this invention contribute to the high level of activity of those formulations in organic and aqueous-organic solvents.

In addition to their activity in organic solvents and aqueous-organic solvents, crosslinked protein crystal formulations according to this invention are particularly resistant to proteolysis, extremes of temperature and extremes of pH. The activity per crosslinked protein crystal unit volume is significantly higher than that of conventionally immobilized proteins or concentrated soluble proteins. This is because protein concentrations within the crosslinked protein crystal components of the formulations are close to theoretical limits.

By virtue of these advantages, the crosslinked protein crystal formulations of the present invention permit a major improvement in reaction efficiency. They provide improved yields under harsh conditions or situations requiring high throughput, enabling process chemists to concentrate on maximizing yield with less concern about reaction conditions.

The protein constituent of the crosslinked protein crystal formulations of this invention may be any protein including, for example, an enzyme or an antibody.

According to one embodiment of this invention, crosslinked protein crystal formulations are characterized by activity in either an organic solvent or an aqueous-organic solvent mixture which is at least about 1.7 times greater than the activity of the equivalent amount of said protein in either crude form or pure form. In an alternate embodiment of this invention, the activity level of such formulations ranges between about 1.7 times and about 90 times greater than the activity of the equivalent amount of said protein in either crude form or pure form.

This invention also includes crosslinked protein crystal formulations characterized by a specific activity per milligram of solid in an organic solvent or an aqueous-organic solvent mixture which is at least about 4.3 times greater than that of said protein in either crude form or pure form. Crosslinked protein crystal formulations according to this invention may also be characterized by a specific activity per milligram of solid in an organic solvent or an aqueous-organic solvent mixture which is between about 4 times and about 442 times greater than that said protein in either crude form or pure form. And crosslinked protein crystal formulations of this invention may also be characterized by a specific activity per milligram of solid in an organic solvent or an aqueous-organic solvent mixture which has a level of activity greater than that of said protein in either crude form or pure form that is selected from the group consisting of at least about 50 times greater, at least about 100 times greater, at least about 200 times greater and at least about 300 times greater activity.

In another embodiment of this invention, crosslinked protein crystal formulations are characterized by activity in an organic solvent or an aqueous-organic solvent mixture which is at least 19 times greater than the activity of crosslinked protein crystals containing no surfactant. Crosslinked protein crystal formulations may also be characterized by activity in an organic solvent or an aqueous-organic solvent mixture which is between about 19 times and about 100 times greater than the activity of crosslinked protein crystals containing no surfactant.

In all of the crosslinked protein formulations described above, the stated activity levels may be exhibited in either organic solvents, or aqueous-organic solvents, or in both solvents. Such activity levels characterize all types of crosslinked protein crystal formulations, including crosslinked enzyme crystal formulations.

The crosslinked protein crystal formulations of this invention may be used in any of a number of chemical processes. Such processes include Industrial and research-scale processes, such as organic synthesis of specialty chemicals and pharmaceuticals, synthesis of intermediates for the production of such products, chiral synthesis and resolution for optically pure pharmaceutical and specialty chemicals. Enzymatic conversion processes include oxidations, reductions, additions, hydrolyses, eliminations, rearrangements, esterifications and asymmetric conversions, including steroselective, stereospecific and regioselective reactions. Products which may be produced using these reactions include chiral organic molecules, peptides, carbohydrates, lipids and other chemical species.

In carrying out any of the above-enumerated reactions, it will be understood by those of skill in the art that the organic solvent or aqueous-organic solvent chosen for the particular reaction should be one which is compatible with the protein constituent of the crosslinked protein crystal, as well as the surfactant used to stabilize the crosslinked protein crystal. Organic solvents may be selected from the group consisting of diols, polyols, polyethers, water soluble polymers and mixtures thereof. Examples of organic solvents include toluene, octane, tetrahydrofuran, acetone, and pyridine. Further examples include hydrophobic or polar organic solvents such as, water miscible or water imiscible solvents, diethylene glycol, 2-methyl-2,4-pentanediol, poly(ethylene glycol), triethylene glycol, 1,4-butanediol, 1,2-butanediol, 2,3,-dimethyl-2,3-butanediol, 1,2-butanediol, dimethyl tartrate, monoalkyl ethers of poly(ethylene glycol), dialkyl ethers of poly(ethylene glycol), and polyvinylpyrrolidone, or mixtures thereof.

According to one embodiment, this invention includes methods for producing a selected product in an organic solvent or an aqueous-organic solvent mixture by combining at least one substrate and at least one protein which acts upon the substrate in the presence of an organic solvent or an aqueous-organic solvent mixture—said protein being a crosslinked protein crystal formulation—and maintaining the combination under conditions which permit said protein to act upon the substrate, thereby producing the selected product. Products which may be produced in such methods include, for example, chiral organic molecules, peptides, carbohydrates and lipids.

Crosslinked protein crystal formulations according to this invention may also be used in methods for purifying or separating a substance or molecule of interest from a sample, by virtue of the ability of the formulation to bind to the substance or molecule of interest. Such separation methods comprise the steps of contacting the crosslinked crystal formulations with the substance or molecule of interest by any means, under conditions which permit said protein to bind with said substance of molecule of interest in said sample to form a complex and separating said complex from said sample. In such methods, the crosslinked protein crystal formulations may be linked to a solid support, packed into a column or layered onto beads.

According to one embodiment of this invention, crosslinked protein crystal formulations may be used as a component of a biosensor for detecting an analyte of interest in a sample, for example, a fluid. Such a biosensor comprises (a) a crosslinked protein crystal formulation, wherein said protein has the activity of acting on the analyte of interest or on a reactant in a reaction in which the analyte of interest participates; (b) a retaining means for said crosslinked protein crystal formulation, said retaining means comprising a material which allows contact between said crosslinked protein crystal formulation and a sample, said sample containing either (1) the analyte upon which the protein acts or (2) a reactant in a reaction in which the analyte participates; and, optionally,(c) a signal transducer which produces a signal in the presence or absence of the analyte. The means for detecting the activity of the protein on the analyte or reactant may be selected from the group consisting of pH electrodes, light sensing devices, heat sensing devices and means for detecting electrical charges. The signal transducer may be selected from the group consisting of optical transducers, electrical transducers, electromagnetic transducers and chemical transducers.

In an alternate embodiment of this invention, crosslinked protein crystal formulations may be used in extracorporeal devices for altering a component of a sample, or for selective degradation or removal of a component of a sample, such as a fluid sample. Such extracorporeal devices comprise (a) a crosslinked protein crystal formulation, wherein the protein has the activity of acting on the component or a reactant in a reaction in which the component participates and (b) a retaining means for said crosslinked protein crystal formulation, said retaining means comprising a material which allows contact between said crosslinked protein crystal formulation and a sample, said sample containing either (1) the component upon which said protein acts or (2) a reactant in a reaction in which the component participates. In such extracorporeal devices, the retaining means may comprise a porous material on which said crosslinked protein crystal formulation is retained or a tube in which said crosslinked protein crystal formulation is present.

Thus, crosslinked protein crystal formulations according to this invention may be advantageously used instead of conventional soluble or immobilized proteins in biosensors and extracorporeal devices. Such uses of the crosslinked protein crystal formulations of this invention provides biosensors and extracorporeal devices characterized by higher degrees of sensitivity, volumeric productivity and throughput than those of biosensors and extracorporeal devices based on conventional soluble or immobilized proteins.

Alternatively, crosslinked protein crystal formulations according to this invention may be used in chromatographic techniques. Such techniques include size exclusion chromatography, affinity chromatography and chiral chromatography. Chromatography of a sample may be carried out in the presence of an organic solvent or an aqueous-organic solvent mixture by contacting said sample with a crosslinked protein crystal formulation under conditions which permit the components of said sample to bind with said protein to form a complex and collecting said components as separate fractions. The crosslinked protein crystal formulation may be contained in a packed chromatography column.

According to another embodiment of this invention, crosslinked crystal protein formulations may be used in gas phase reactors, such as catalytic convertors for gas phase reactions. For example, gas may be passed through a column packed with a crosslinked protein formulation—which degrades the gas.

Crosslinked protein crystal formulations according to this invention may also be used in various environmental applications. They may be used in place of conventional soluble or immobilized proteins for environmental purposes, such as cleaning-up oil slicks. For example, one or more organic solvents may be added to the oil slick, followed by a crosslinked protein crystal formulation.

Crosslinked protein crystal formulations according to the present invention may also be used for air purification in conjunction wish air filtration. For example, air may be passed through a column packed with a crosslinked protein formulation to degrade and filter out any unwanted contaminants.

This invention also includes methods for increasing the activity of crosslinked protein crystals in an organic solvent or an aqueous-organic solvent mixture comprising the steps of combining the crosslinked protein crystals with a surfactant to produce a combination and drying the combination of crosslinked protein crystals and surfactant in the presence of an organic solvent to form a crosslinked protein crystal formulation.

Alternatively, crosslinked protein crystal formulations according to this invention may be used as ingredients in topical creams and lotions, for skin protection or detoxification. They may also be used as anti-oxidants in cosmetics.

According to this invention, any individual, including humans and other mammals, may be treated in a pharmaceutically acceptable manner with a catalytically effective amount of a crosslinked protein crystal formulation for a period of time sufficient to protect, repair or detoxify the area to which it is applied. For example, crosslinked protein crystal formulations may be topically administered to any epithelial surface. Such epithelial surfaces include oral, ocular, aural, nasal surfaces.

The crosslinked protein crystal formulations may be in a variety of conventional depot forms employed for topical administration to provide reactive topical compositions. These include, for example, semi-solid and liquid dosage forms, such as liquid solutions or suspensions, gels, creams, emulsions, lotions, slurries, powders, sprays, foams, pastes, ointments, salves, balms and drops. Compositions comprising crosslinked protein crystal formulations may also comprise any conventional pharmaceutically acceptable carrier or adjuvant. These carriers and adjuvants include, for example, ion exchangers, alumina, aluminum stearate, lecithin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, sodium chloride, zinc salts, colloidal silica, magnesium, trisilicate, cellulose-based substances and polyethylene glycol. Adjuvants for topical or gel base forms may include, for example, sodium carboxymethylcellulose, polyacrylates, polyoxyethylele-polyoxypropylene-block polymers, polyethylene glycol and wood wax alcohols.

Alternatively, crosslinked protein crystal formulations may be formulated into a health care device selected from the group consisting of dressings, sponges, strips, plasters, bandages, patches or gloves.

The most effective mode of administration and dosage regimen will depend upon the effect desired, previous therapy, if any, the individual's health status and response to the crosslinked protein crystal formulation and the judgment of the treating physician. The crosslinked protein crystal formulation may be administered in any pharmaceutically acceptable topical dosage form, at one time or over a series of treatments.

The amount of the crosslinked protein crystal formulation that may be combined with carrier materials to produce a single dosage form will vary depending upon the particular mode of topical administration, formulation, dose level or dose frequency. A typical preparation will contain between about 0.1% and about 99%, preferably between about 1% and about 10%, crosslinked protein crystal formulation (w/w).

Upon improvement of the individual's condition, a maintenance dose of crosslinked protein crystal formulation may be administered, if necessary. Subsequently, the dosage or frequency of administration, or both, may be reduced as a function of the symptoms, to a level at which the improved condition is retained. When the symptoms have been alleviated to the desired level, treatment should cease. Individuals may, however, require intermittent treatment on a long-term basis upon any recurrence of symptoms.

According to the present invention, preparation of crosslinked protein crystal formulations includes the steps of crystallizing and crosslinking the protein, which may be carried out as described in PCT patent application WO92/02617, which is incorporated herein by reference. Alternatively, crosslinked protein crystal formulations may be prepared as illustrated below for crosslinked enzyme crystal formulations.

Preparation of Crosslinked Enzyme Crystal Formulations—Enzyme Crystallization

Enzyme crystals are grown by the controlled precipitation of enzyme out of aqueous solution or aqueous solution-containing organic solvents. Conditions to be controlled include, for example, the rate of evaporation of solvent, the presence of appropriate co-solutes and buffers, pH and temperature. A comprehensive review of the various factors affecting the crystallization of proteins has been published by McPherson, *Methods Enzymol.*, 114, pp. 112–20 (1985).

McPherson and Gilliland, *J. Crystal Growth*, 90, pp. 51–59 (1988) have compiled comprehensive lists of proteins and nucleic acids that have been crystallized, as well as the conditions under which they were crystallized. A compendium of crystals and crystallization recipes, as well as a repository of coordinates of solved protein and nucleic acid crystal structures, is maintained by the Protein Data Bank at the Brookhaven National Laboratory [Bernstein et al., *J. Mol. Biol.*, 112, pp. 535–42 (1977)]. These references can be used to determine the conditions necessary for crystallization of an enzyme previously crystallized, as a prelude to the formation of an appropriate crosslinked enzyme crystal, and can guide the crystallization strategy for other enzymes. Alternatively, an intelligent trial and error search strategy can, in most instances, produce suitable crystallization conditions for many enzymes, provided that an acceptable level of purity can been achieved for them [see e.g., C. W. Carter, Jr. and C. W. Carter, *J. Biol. Chem.*, 254, pp. 12219–23 (1979)].

Enzymes which may be crystallized to form the crosslinked enzyme crystal component of the formulations according to this invention include hydrolases, isomerases, lyases, ligases, transferases and oxidoreductases. Examples of hydrolases include thermolysin, elastase, esterase, lipase, nitrilase, hydantoinase, asparaginase, urease, subtilisin and other proteases and lysozyme. Examples of lyases include aldolases and hydroxynitril lyase. Examples of oxidoreductases include glucose oxidase, alcohol dehydrogenase and other dehydrogenases.

For use in crosslinked enzyme crystal formulations according to this invention, the large single crystals which are needed for X-ray diffraction analysis are not required. Microcrystalline showers are suitable.

In general, crystals are produced by combining the enzyme to be crystallized with an appropriate aqueous solvent or aqueous solvent containing appropriate precipitating agents, such as salts or organics. The solvent is combined with the protein at a temperature determined experimentally to be appropriate for the induction of crystallization and acceptable for the maintenance of enzyme activity and stability. The solvent can optionally include co-solutes, such as divalent cations, co-factors or chaotropes, as well as buffer species to control pH. The need for co-solutes and their concentrations are determined experimentally to facilitate crystallization. In an industrial scale process, the controlled precipitation leading to crystallization can best be carried out by the simple combination of protein, precipitant, co-solutes and, optionally, buffers in a batch process. Alternative laboratory crystallization methods, such as dialysis or vapor diffusion can also be adapted. McPherson, supra, and Gilliland, supra, include a comprehensive list of suitable conditions in their reviews of the crystallization literature. Occasionally, incompatibility between the crosslinking reagent and the crystallization medium might require exchanging the crystals into a more suitable solvent system.

Many of the enzymes for which crystallization conditions have already been described, have considerable potential as practical catalysts in industrial and laboratory chemical processes and may be used to prepare crosslinked enzyme crystal formulations according to this invention. It should be noted, however, that the conditions reported in most of the above-cited references have been optimized to yield, in most instances, a few large, diffraction quality crystals. Accordingly, it will be appreciated by those of skill in the art that some degree of adjustment of these conditions to provide a high yielding process for the large scale production of the smaller crystals used in making crosslinked enzyme crystals may be necessary.

Preparation of Crosslinked Enzyme Crystal Formulations—Crosslinking of Enzyme Crystals Once enzyme crystals have been grown in a suitable medium they can be crosslinked. Crosslinking results in stabilization of the crystal lattice by introducing covalent links between the constituent enzyme molecules of the crystal. This makes possible the transfer of enzyme into an alternate reaction environment that might otherwise be incompatible with the existence of the crystal lattice or even with the existence of intact protein. Crosslinking can be achieved by a wide variety of multifunctional reagents, including bifunctional reagents. According to a preferred embodiment of this invention, the crosslinking agent is glutaraldehyde. For a representative listing of other available crosslinking reagents see, for example, the 1990 catalog of the Pierce Chemical Company.

Crosslinking with glutaraldehyde forms strong covalent bonds primarily between lysine amino acid residues within and between the enzyme molecules in the crystal lattice. The crosslinking interactions prevent the constituent enzyme molecules in the crystal from going back into solution, effectively insolubilizing or immobilizing the enzyme molecules into microcrystalline particles (preferably having lengths which are, on average, less than or equal to $10^{-1}$ mm).

Preparation of Crosslinked Enzyme Crystal Formulations—Exposure of Crosslinked Enzyme Crystals to Surfactants Crosslinked enzyme crystals prepared as described above, may be used to prepare enzyme crystal formulations for reactions in organic solvents and aqueous-organic solvent mixtures by being contacted with a surfactant. After exposure of the crosslinked enzyme crystals to the surfactant and subsequent drying in the presence of an organic solvent, the resulting crosslinked enzyme crystal formulation is particularly active and stable in organic solvents and aqueous-organic solvent mixtures. The details described below with respect to crosslinked enzyme crystal formulations and their production are equally applicable to crosslinked protein crystal formulations.

Surfactants useful to prepare crosslinked enzyme crystal formulations according to this invention include cationic, anionic, non-ionic or amphoteric, or mixtures thereof. The preferred surfactant will depend upon the particular enzyme component of the crosslinked enzyme crystals to be used to prepare the crosslinked enzyme crystal formulation. This may be determined by carrying out a routine screening procedure based on a reaction catalyzed by the particular enzyme. Such screening procedures are well known to those of skill in the art. Illustrative screening processes are set forth in Examples 6–8.

Examples of useful cationic surfactants include amines, amine salts, sulfonium, phosphonium and quarternary ammonium compounds. Specific examples of such cationic surfactants include:

Methyl trioctylammonium chloride (ALIQUAT 336)
N,N',N'-polyoxyethylene(10)-N-tallow-1,3-diaminopropane
(EDT-20,' PEG-10 tallow).

Useful anionic surfactants include, for example, linear alkylbenzene sulphonate, alpha-olefin sulphonate, alkyl sulphate, alcohol ethoxy sulfate, carboxylic acids, sulfuric esters and alkane sulfonic acids. Examples of anionic surfactants include:

TRITON QS-30 (Anionic octyl phenoxy polyethoxyethanol)
Aerosol 22
dioctyl sulfosuccinate (AOT)
Alkyl Sodium Sulfate (Niaproof):
  Type-4
  Type-8
Alkyl (C9–C13) Sodium Sulfates (TEEPOL HB7).

Non-ionic surfactants useful for stabilization include nonyl phenol ethoxylate, alcohol ethoxylate, sorbitan trioleate, non-ionic block copolymer surfactants, polyethylene oxide or polyethylene oxide derivatives of phenol alcohols or fatty acids. Examples of non-ionic surfactants include:

Polyoxyethylene Ethers:
  4 lauryl Ether (BRIJ 30)
  23 lauryl Ether (BRIJ 35)
Octyl Phenoxy polyethoxyethanol (TRITONS):
  Tx-15
  Tx-100
  Tx-114

Tx-405
DF-16
N-57
DF-12
CF-10
CF-54
Polyoxyethylenesorbitan:
   Monolaurate (TWEEN 20)
Sorbitan:
   Sesquioleate (ARLACEL 83)
   Trioleate (SPAN 85)
Polyglycol Ether (Tergitol):
   Type NP-4
   Type NP-9
   Type NP-35
   Type TMN-10
   Type 15-S-3
   Type TMN-6(2,6,8, Trimethyl-4-nonyloxypolyethylenoxyethanol
   Type 15-S-40.

Generally, in order to prepare crosslinked enzyme crystal formulations, the surfactant should be added to a crosslinked enzyme crystal-containing solution in an amount sufficient to allow the surfactant to equilibrate with and/or penetrate the crosslinked enzyme crystals. Such an amount is one which provides a weight ratio of crosslinked enzyme crystals to surfactant between about 1:1 and about 1:5, preferably between about 1:1 and about 1:2. The crosslinked enzyme crystals are contacted with surfactant for a period of time between about 5 minutes and about 24 hours, preferably between about 30 minutes and about 24 hours. Following that contact, the crosslinked enzyme crystal/surfactant combination may be dried in the presence of an organic solvent to form the crosslinked enzyme crystal formulation.

The choice co organic solvent and length of drying time will depend on the particular crosslinked enzyme crystals and the particular surfactant used to produce the crosslinked enzyme crystal formulations. Nevertheless, the solvent and drying time should be those which provide a crosslinked enzyme crystal formulation characterized by a water content that permits the formulation to have maximum activity and stability in organic solvents or aqueous-organic solvent mixtures. According to one embodiment of this invention, the drying time may be between about 5 minutes and about 24 hours, preferably between about 30 minutes and about 24 hours. The organic solvent used in the drying step may be present in an amount between about 10 wt % and about 90 wt % of the total mixture, preferably between about 40 wt % and about 80 wt % of the total mixture.

Alternatively, the crosslinked enzyme crystal/surfactant combination may be lyophilized in the presence of an organic solvent. Lyophilization may be carried out for a period of time between about 30 minutes and about 18 hours.

The resulting crosslinked enzyme crystal formulation should contain between about 10 wt % and about 70 wt % of surfactant, by weight of the final formulation, preferably between about 25 wt % and about 45 wt % of surfactant, by weight of the final formulation.

In order that this invention may be better understood, the following examples are set forth. These examples are for the purpose of illustration only and are not to be construed as limiting the scope of the invention in any matter.

EXAMPLES

Example 1

Preparation of A Crosslinked LPS Crystal Formulation

A slurry of 15 kg crude *Pseudomonas cepacia* lipase (PS 30 lipase—AMANO) ("LPS") was dissolved in 100 L distilled deionized water and the volume brought to 200 L with additional distilled deionized water. The suspension was mixed in an Air Drive Lightning mixer for 2 hours at room temperature and then filtered through a $0.5\mu$ filter to remove celite. The mixture was then ultrafiltered and concentrated to 10 L (121.4 g) using a 3K hollow fiber filter membrane cartridge. Solid calcium acetate was added to a concentration of 20 mM $Ca(CH_3COO)_2$. The pH was adjusted to 5.5 with concentrated acetic acid, as necessary. The mixture was heated to and maintained at a temperature of 30° C. Magnesium sulfate was added to a 0.2 M concentration followed by glucopon to a 1% concentration. Isopropanol was then added to a final concentration of 23%. The resulting solution was mixed for 30 minutes at 30° C., then cooled from 30° C. to 12° C. over a 2 hour period. Crystallization was then allowed to proceed for 16 hours.

The crystals were allowed to settle and soluble protein was removed using a peristaltic pump with tygon tubing having a 10 ml pipette at its end. Fresh crystallization solution (23% isopropyl alcohol, 0.2 M $MgSO_4$, 1% glucopon, 20 mM $Ca(CH_3COO)_2$, pH 5.5) was added to bring the concentration of protein to 30 mg/ml (O.D. 280 of a 1 mg/ml solution=1.0, measured using a spectrophotometer at wavelength 280). The crystal yield was about 120 grams. The crystal solution was then crosslinked as follows.

A 2 liter aliquot of crosslinking agent was prepared by mixing 1 volume of 50% glutaraldehyde with 4 volumes of 0.1 M Tris (pH 9.25). Crosslinking was then carried out using 13.5 ml crosslinking agent per gram of enzyme. More particularly, a 0.4 ml aliquot of the crosslinking agent was then added to 1 ml of enzyme slurry (30 mg/ml), over a total addition time of 2 hours. The mixture was allowed to stand for 8 hours at room temperature for crosslinking. The crosslinking reaction was stopped by washing the crosslinked crystals extensively in a filter press with an approximately 1.5 crystal slurry volume of buffer (10 mM Tris, 10 mM $CaCl_2$, pH 7.0).

A 30 gram aliquot of the above-prepared crosslinked LPS enzyme crystals was suspended in 340 ml storage buffer (10 mM Tris, 10 mM $CaCl_2$, pH 7.0) and the mixture poured into a sintered glass funnel (porosity ~10–20$\mu$) at room temperature. The enzyme crystals were exposed to the surfactant EDT-20; PEG-10 tallow aminopropylamine as described below. This surfactant was selected by the screening process set forth in Example 6, infra.

The buffer above the crosslinked LPS crystals was filtered in a sintered glass funnel (described above), keeping the enzyme crystals wet throughout the process. The height of the crosslinked enzyme crystals in the funnel was measured and found to be 60 ml. The surfactant N, N', N-polyoxyethylene (10)-N-tallow-1,3-diaminopropane (EDT-20', PEG-10 tallow) was added together with the solvent 2-butanone, such that the ratio of surfactant-:crosslinked enzyme crystals was 1:1 (30 g surfactant:30 g LPS=30 ml). This was done by pouring a mixture of 30 ml 2-butanone and 30 ml surfactant, for a total of 60 ml, on top of the crosslinked enzyme crystals. A gentle suction was applied to ensure that the crosslinked enzyme crystals were coated with the surfactant and so that the enzyme cake did not dry. After 30 minutes at room temperature, the mixture was then transferred to a drying vessel (a fritted pressure filter funnel) in a stream of air to a water content of about 1–3%, as determined by Karl Fisher titration.

LPS crosslinked crystal formulations according to this invention may also be prepared using crosslinked LPS crystals sold under the trade name ChiroCLEC-PC, which are available from Altus Biologics, Inc. (Cambridge, Mass.).

Example 2

Preparation of A Crosslinked CRL Crystal Formulation

A 5 kg aliquot of *Candida rugosa* lipase ("CRL") in powder form (AMANO) was mixed with 5 kg celite and dissolved in 102 L distilled deionized water and the volume brought to 200 L with distilled deionized water. The suspension was mixed in an Air Drive Lightning mixer for 2 hours at room temperature and then filtered through a 0.5 micron filter to remove celite. The mixture was then ultra-filtered and concentrated to 14 L (469 g) using a 3K hollow fiber filter membrane cartridge. Solid calcium acetate was added to a concentration of 5 mM $Ca(CH_3COO)_2$. The pH was adjusted to 4.8 with concentrated acetic acid, as necessary. The mixture was heated to and maintained at a temperature of 25° C. A 3.5 L aliquot of (100%) 2-methyl-2,4-pentanediol "MPD" and crystal seeds (0.5 g protein) were added. The resulting solution was mixed overnight. Crystallization was then allowed to proceed overnight, for about 17–20 hours.

The crystals were allowed to settle and soluble protein was removed using a peristalic pump with tygon tubing having a 10 ml pipette at its end. Fresh crystallization solution (20% MPD, 5 mM $Ca(CH_3COO)^2$, pH 4.8) was added to bring the concentration of protein to 35 mg/ml (O.D. 280 of a 1 mg/ml solution=1.0). This step was then repeated. The crystal yield was about 217 grams. The crystal solution was then crosslinked as follows.

Crosslinking agent was prepared by mixing 1 volume of 50% glutaraldehyde with 1 volume of 0.3 M sodium borate buffer (pH 9.0) and heating the mixture for 1 hour at 60° C. The mixture was then allowed to stand until it cooled to room temperature, with the pH being adjusted to 6.0, as necessary, using HCl. Crosslinking was carried out using 3.885 ml (1.949 g) of crosslinking agent, per gram of enzyme. More particularly, a 1686 ml aliquot of the crosslinking agent was then added to 217 g of enzyme slurry by pumping the crosslinking agent slowly, for a total addition time of 2 hours. The mixture was then let stand at room temperature for an additional 16 hours for crosslinking. The crosslinking reaction was stopped by washing the crosslinked crystals extensively in a Buchner funnel with a $1\mu$ filter, first with 30 L water then with 2 M sodium chloride and buffer (10 mM Tris, 10 mM $CaCl_2$, pH 7.0).

A 6 gram aliquot of the above-prepared crosslinked CRL enzyme crystals was suspended in 100 ml storage buffer (10 mM Tris, 10 mM $CaCl_2$, pH 7.0) and the mixture poured into a sintered glass funnel (porosity ~10–20$\mu$) at room temperature. The buffer was then removed from the enzyme. The enzyme crystals were exposed to the surfactant tergitol type TMN-6 as described below. This surfactant was selected by the screening process set forth in Example 8, infra.

The buffer above the crosslinked CRL crystals was filtered in a sintered glass funnel (as described above), keeping the crosslinked enzyme crystals wet throughout the process. The height of the crosslinked enzyme crystals in the funnel was measured and found to be 34 ml. The surfactant was added together with the solvent 2-butanone, such that the ratio of surfactant:crosslinked enzyme crystals was 1:1 (6 g CRL:6 g surfactant=5.7 ml). This was done by pouring a mixture of 28.3 ml 2-butanone and 5.7 ml surfactant, for a total of 34 ml, on top of the crosslinked enzyme crystals. A gentle suction was applied to ensure that the crosslinked enzyme crystals were coated with the surfactant and so that the enzyme cake did not dry. After 30 minutes at room temperature, the mixture was then transferred to a drying vessel (a fritted pressure filter funnel) in a stream of air to a water content of about 7–13%, as determined by Karl Fisher titration.

CRL crosslinked crystal formulations according to this invention may also be prepared using crosslinked CRL crystals sold under the trade name X ChiroCLEC-CR (crosslinked *Candida rugosa* lipase microcrystals), which are available from Altus Biologics, Inc. (Cambridge, Mass.).

Example 3

Preparation of A Crosslinked ABL Crystal Formulation

A slurry of 30 kg or 25 L of *Bacillus licheniformis* subtilisin A ("ABL") (ALCALASE) was mixed in an Air Drive Lightning mixer with 50 L of 15% $Na_2SO_4$ (pH 5.5). Crystal seeds (0.27 g protein) were added, and the mixture maintained at a temperature of 30° C. Crystallization was then allowed to proceed for a period of 3–4 days. The mother liquor was removed using a Buchner funnel with a $1\mu$ filter.

The crystals were washed with 50 L of 15% $Na_2SO_4$ (pH 5.5) and then suspended in 40 L of 15% $Na_2SO_4$ (pH 5.5). The crystal yield was about 1069 grams. The crystal solution was then crosslinked as follows.

Crosslinking was carried out using 1.68 ml of 50% glutaraldehyde crosslinking agent per gram of enzyme. More particularly, a 1796 ml aliquot of crosslinking agent was added to 1069 g enzyme over a total addition time of 30 minutes to 1 hour. The mixture was allowed to mix for 4 hours at room temperature for crosslinking, keeping the pH at 5.5 at all times. The crosslinking reaction was stopped by washing the crosslinked crystals extensively in a filter press with water until the conductivity of washing was 2 ms/cm. Then the crosslinked enzyme crystals were suspended in buffer (0.1 NaAc, 20 mM $CaCl_2$, pH 5.7).

A 20 gram aliquot of the above-prepared crosslinked ABL enzyme crystals was suspended in 100 ml storage buffer (0.1 NaAc, 20 mM $CaCl_2$, pH 5.7) and the mixture poured into a sintered glass funnel (porosity ~10–20$\mu$) at room temperature. The enzyme crystals were exposed to the surfactant TERGITOL (polyglycolether) type 15-S-3 as described below. This surfactant was selected by the screening process set forth in Example 7, infra.

The buffer above the crosslinked ABL crystals was filtered in a sintered glass funnel (as described above), keeping the crosslinked enzyme crystals wet throughout the process. The height of the crosslinked enzyme crystals in the funnel was measured and found to be 50 ml. The surfactant was added together with the solvent isopropanol, such that the ratio of surfactant:crosslinked enzyme crystals was 1:1.5 (30 g ABL:30 ml surfactant=50 ml). This was done by pouring a mixture of 20 ml isopropanol and 30 ml surfactant, for a total of 50 ml, on top of the crosslinked enzyme crystals. A gentle suction was applied to ensure that the crosslinked enzyme crystals were coated with the surfactant and so that the enzyme cake did not dry. After 30 minutes at room temperature, the mixture was then transferred to a drying vessel (a fritted pressure filter funnel) in a stream of air to a water content of about 1–4%, as determined by Karl Fisher titration.

Alternatively, 15 g of wet cake of ABL crosslinked enzyme crystals may be mixed with 20 g surfactant and 30 ml isopropanol. The mixture may then be incubated for 30 minutes. Subsequently, solvent and surfactant may be removed by suction, as described above. The wet crosslinked enzyme crystals may then be transferred to a lyophilization vessel and frozen in acetone in dry ice for 30 minutes. Then, the lyophilization vessel is transferred to the lyophilizer and let go for 30 minutes.

Lyophilized crosslinked enzyme crystal formulations prepared as described above may be stored at room temperature or at 4° C., prior to their use in organic solvents. Lyophilized crosslinked enzyme crystal formulations may be stored at room temperature.

ABL crosslinked crystal formulations according to this invention may also be prepared using crosslinked ABL crystals sold under the trade name ChiroCLEC-BL (crosslinked *Bacillus licheniformis* Subtilisin microcrystals), which are available from Altus Biologics, Inc. (Cambridge, Mass).

Example 4

Activity of Crosslinked Enzyme Crystal Formulations in Organic Solvents

The activities of the crosslinked enzyme crystal formulations, as prepared above, or their crude enzyme counterparts, in the resolution of alcohols, acids and amines are presented in Table 1. Enzyme activity was assayed by HPLC and gas chromatography ("GC"). The particular resolutions generating the data in Table 1 were carried out as described below.

Resolution of (+/−) Menthol by Transesterification

A solution of (+/−) Menthol (449 mM) in 1 ml of toluene containing 7.5 μl (0.15%) $H_2O$ was stirred with 4 mg of the crosslinked CRL crystal formulation prepared in Example 2 for 5 minutes, until a fine suspension was attained. Vinyl acetate (449 mM) was added and the resulting suspension was stirred at 25° C. for 4 hours, at which time capillary gas chromatography ("GC") analysis indicated 15% conversion. The GC conditions were as follows: DB1701 15 m×0.25 mm GC Column, 25 mm film thickness (J & W Scientific, Folsom Calif.); helium flow at 25 cm/sec; Temperature program: Initial=119° C. for 1 minute, Gradient$_1$ rate=5° C./min to 130° C. for 0.3 minutes, Gradient$_2$ rate=70° C./min to 175° C. for 1.86 minute. Retention times: 2.85 minutes [(+) Menthol], 4.77 minutes [ester]. The reaction was halted by suction filtration of the catalyst. The optical purity of the product ester was determined to be 99.4% enantiomeric excess ("ee") by GC analysis.

The chiral GC conditions were as follows: Cyclodex B 25 m capillary GC Column, 25 mm i.d. (J & W Scientific, Folsom Calif.); $N_2$ flow at 1 ml/min; Temperature program: Initial=90° C. for 5 min, Gradient rate=1° C./min, Final=115° C. for 10 minutes. Retention times: 24.90 minutes [(+) Menthol], 25.40 minutes [(−) Menthol], 35.97 minutes [(−) ester], 36.11 minutes [(+) ester].

Esterification of Ibuprofen with n-Amyl Alcohol (R,S)-Ibuprofen (97 mM) was dissolved in 1 ml of isooctane. To this solution was added 460 mM of n-amyl alcohol and 1 mg of the crosslinked CRL crystal formulation prepared in Example 2. The suspension was stirred at room temperature and the production of n-amyl Ibuprofen was followed by chiral HPLC. After 24 hours, the conversion had reached 28%.

The chiral HPLC conditions were as follows: Acid: (R,R) Whelk-O1, (Regis Technologies, Morton Grove, Ill.) 5 mm, 100 Å, 25 cm column. Mobile phase=hexane 0.5% acetic acid. Over a 30 minute period, hexane without acetic acid was substituted (at an even rate) for the acidified hexane. Helium flow rate=1 ml/min., UV detection at 254 nm. Retention times: 16.7 and 19.2 minutes for the ester, 21.8 and 28.1 minutes for the acid.

Resolution of (R,S)-2-Hydroxyhexanoic Acid by Esterification

To a solution of (R,S) 2-hydroxyhexanoic acid (532 mM) in 1 ml of toluene containing n-BuOH (1060 mM) was added 10 mg of the crosslinked CRL crystal formulation prepared in Example 2. The resulting mixture was magnetically stirred at 25° C. for 1 hour, at which time capillary GC analysis indicated 46% conversion. The GC conditions were as follows: DB1701 15 m×0.25 mm GC Column, 25 mm film thickness (J & W Scientific, Folsom Calif.); helium flow at 25 cm/sec; Temperature program: Initial=110° C. for 5 minutes, Gradient rate=20° C./min to 200° C. Sample preparation: 10 μl of reaction mixture in 1 ml hexane with 100 μl MeOH and 100 μl TMS-diazomethane-2M in hexane. Retention times: 2.12 minutes [methyl ester], 6.46 minutes [butyl ester]. The reaction was halted by suction filtration of the catalyst. Optical purity of the butyl ester and the acid (as its methyl ester) were determined by chiral GC analysis.

The chiral GC conditions were as follows: Cyclodex B 25 m capillary GC Column, 25 mm i.d.(J & W Scientific, Folsom Calif.); $N_2$ flow at 1 ml/min; Temperature program: Initial=80° C. for 30 minutes, Gradient rate 5° C./min, Final=170° C. for 10 minutes. Retention times: 27.80 minutes [R-methyl ester], 31.03 minutes [S-methyl ester], 44.30 minutes [R-butyl ester] and 44.50 minutes [S-butyl ester].

Resolution of Phenethyl Alcohol by Transesterification

To 200 mM phenethyl alcohol and 200 mM vinyl acetate in 1 ml toluene was added 1.2 mg of the crosslinked LPS crystal formulation prepared in Example 1 and the reaction mixture stirred at room temperature for 30 minutes. The catalyst was removed by centrifugation to stop the reaction. Conversion and optical purity were determined by chiral GC.

The chiral GC conditions were as follows: Cyclodex capillary GC 25 m column, 25 mm i.d. (J & W Scientific, Folson, Cailf.) $N_2$ flow at 1 ml/min. Temperature program: Initial 100° C. for 4 minutes, Gradient rate 5° C./min., to 135° C. and 2 minutes at 135° C., 2° C./min to 144° C. and 5 minutes at 144° C., 5° C./min to 150° C. and 2 minutes at 150° C. Retention times: 12.08 and 12.47 for (S) and (R) ester, respectively; 12.25 and 12.55 min for (R) and (S) alcohol, respectively. Conversion was found to be 41.7% and the ee of product and substrate in this conversion was found to be 98.53 and 70.42%, respectively, with an E value of 297. E was calculated according to C. S. Chen et al., *J. Am. Chem. Soc.,* 104, pp. 7294–99 (1982). See J. J. Lalonde et al., *J. Am. Chem. Soc.,* 117, pp. 6815–52 (1995) for a discussion of the applicability of E for reactions affected by inhibition or catalyzed by crude enzymes.

Resolution of (±)-Sulcatol

To a solution of 80 mM (±)-Sulcatol and 120 mM vinyl acetate in 1 ml of toluene was added 4 mg of the crosslinked LPS crystal formulation prepared in Example 1. The mixture was stirred at room temperature for 20 hours. The catalyst was then removed by filtration. The optical purity of product and remaining starting material were directly analyzed by GC using a chiral GC column. The ee of the remaining starting material and product alcohol was >98% and 51.3%, respectively.

The chiral GC conditions were as follows: CYCLODEX B capillary GC 25 m column, 25 mm i.d. (J & W Scientific, Folsom, Calif.), helium flow at 1 ml/min. Temperature program: Initial: 90° C. for 10 minutes, Gradient rate: 5° C. per minute, Final 130° C. for 20 minutes. Retention time: (S)-sulcatol, 12.50 minutes; (R)-sulcatol, 12.32 minutes; (S)-sulcatol acetate, 14.43 minutes; (R)-sulcatol acetate, 15.12 minutes. The conversion was 66.1%. The E value was calculated to be 27.

Resolution of (±)-2-Octanol

To a solution of 80 mM (±)-2-octanol and 120 mm vinyl acetate in 1 ml of toluene was added 4 mg of the crosslinked LPS crystal formulation prepared in Example 1. The mixture was stirred at room temperature for 4 hours. The catalyst was then removed by filtration. The optical purity of the acetate product was directly analyzed by GC using a chiral GC column. The ee was determined to be 63.0%. The remaining alcohol was converted to its corresponding butyrate by reaction with butyric anhydride in pyridine. The optical purity of the butyrate derivative was then analyzed with GC. The ee was 83.7%.

The chiral GC conditions were as follows: CYCLODEX B capillary GC 25 m column, 25 $\mu$m i.d. (J & W Scientific, Folsom, Calif.), helium flow at 1 ml/min. Temperature program: Initial=90° C. for 10 minutes, Gradient rate 2° C. per minute. Final 130° C. for 20 minutes. Retention time: (S)-2-octanol acetate, 15.66 minutes; (R)-2-octanol acetate, 16.93 minutes; (S)-2-octanol butyrate, 26.49 minutes; (R)-2-octanol butyrate, 26.95 minutes. The conversion was 57.1%. The E value was calculated to be 9.8.

Resolution of Tryptamine

A solution of 200 mM tryptamine and 400 mM 2,2,2-trifluoroethyl butanoate in 1 ml of tert-butanol was incubated with 16 mg of the crosslinked ABL crystal formulation prepared in Example 3 on a rotary shaker at 40° C. When the desired level of conversion was reached, the catalyst was removed by centrifugation and washed with ethyl acetate. The combined organic mixtures were evaporated in vacuo to give a residue which was then purified by silica gel column chromatography to give the remaining tryptamine and the butyl amide product. The optical purity of the butyl amide product was directly analyzed by chiral HPLC. The remaining amine was converted to its urethane derivative by treatment with methyl chloroformate and analyzed for optical purity by chiral HPLC: ee=94% at 20% conversion; R-alphamethyltryptamine; ee>98, at 53% conversion.

The chiral HPLC conditions were as follows: CHIRACEL OJ 25 cm column (Chiral Technologies, Exton, Pa., a division of Daicel Chemical Inc.), for butyl amide; mobile phase=80% hexane (with 0.1% TFA), 20% isopropanol (with 0.1% TFA), helium flow rate=1 ml/min., UV detection at 254 nm. Retention times: D-butyl amide product, 9.3 minutes and L-butyl amide product, 11.2 minutes. D-urethane derivative, 24.8 minutes and L-urethane derivative, 27.6 minutes.

Each of the resolutions described above, was carried out with the crude enzyme counterpart to the crosslinked enzyme crystal formulation, using the enzyme concentrations listed in footnote (b) to Table 1 below.

TABLE 1

Enzyme-Catalyzed Resolutions in Organic Solvents

| Compound | Acylating agent and solvent | Enzyme | $^v$crosslinked enzyme$^a$ crystal, × 10$^3$ | $^v$crude$^b$, enzyme × 10$^3$ | $^v$Crosslinked enzyme crystal/$^v$crude; equal protein | E Crosslinked enzyme crystal | E crude enzyme |
|---|---|---|---|---|---|---|---|
| Menthol [449 mM] | VA [449 mM] in toleune | CRL | 1220 | 4 | 62 | >>100 | 16 |
| Ibuprofen [97 mM] | n-amyl alcohol [460 mM] in isooctane | CRL | 57.5 | 0.13 | 90 | >>100 | 7.2 |
| Hydroxy hexanoic acid [532 mM] | BuOH [1060 mM] in toluene | CRL | 85 | 2.2 | 7.9 | 55 | 2 |
| Sec-phenethyl alcohol [200 mM] | VA [200 mM] in toluene | LPS | 15000 | 90 | 1.7 | >>100 | >>100 |
| Sulcatol [80 mM] | VA [120 mM] in toluene | LPS | 6700 | 20 | 3.4 | 28 | 35 |
| 2-Octanol [80 mM] | VA [120 mM] in toluene | LPS | 11700 | 44.5 | 2.6 | 9.8 | 9.9 |
| Methyl tryptamine [200 mM] | TFB [400 mM] in tert-BuOH | ABL | 12.5 | 2.9 | 3.6 | 41 | 46 |

$^a$Crosslinked enzyme crystal concentrations were 4, 1, 10, 1.2, 0.4, 0.4 and 16 mg/ml.
$^b$Crude enzyme concentrations were 20, 15, 50, 8.3, 40, 40 and 28 mg/ml, respectively, going from top to bottom of the table.

In Table 1, rates are displayed in $\mu$mol/min×mg at 25° C. and concentrations are shown in brackets.

In column 2 of the table, "VA" denotes vinyl acetate and "TFB" denotes trifluoroethyl butyrate. In column 3, the water content of the crude enzyme preparations was 9.3%, 2.5% and 5% for CRL, LPS and ABL, respectively.

In column 4 of Table 1, the water content of the crosslinked enzyme crystal formulations was 13.3%, 2.3% and 2.5% for CRL, LPS and ABL, respectively. The amount of surfactant in the final preparations of crosslinked enzyme crystal formulations were 16%, 40% and 50% (w/w) for CRL, LPS and ABL, respectively.

In column 6 of Table 1, the total protein content in the crude preparations of CRL, LPS and ABL were 10%, 0.7% and 7%, respectively. The protein content of crude ABL was 50% (w/w).

In column 7, reaction rates and enantio-selectivities were assayed by CYCLODEX B, (R,R)Whelk-O1 (Ibuprofen) GC and CHIRACEL OJ (methyltryptamine) columns. E was calculated according to C. S. Chen et al., *J. Am. Chem. Soc.*, 104, pp. 7294–99 (1982). See J. J. Lalonde et al., *J. Am. Chem. Soc.*, 117, pp. 6845–52 (1995) for a discussion of the applicability of E for reactions affected by inhibition or catalyzed by crude enzymes.

In column 8, $E_{app}$ was calculated as in an irreversible case based on the enantiomeric excess of the product at low conversion.

As demonstrated in Table 1, the crosslinked enzyme crystal formulations of three different enzymes (two lipases and subtilisin) and their crude counterparts exhibited markedly different activity in the presence of organic solvents. The crosslinked enzyme crystal formulations were much more active than their crude counterparts on a weight basis (columns 4 and 5), and in all of the reactions, their specific activity per mg of protein was higher as well (column 6). Thus, in order to achieve the same activity in the resolution of menthol or sulcatol, for example, it is possible to use about 300 fold less catalyst. In the case of CRL and ABL, the striking difference in activities between the crude enzyme preparations and the crosslinked enzyme crystal formulations cannot be attributed to differences in water content. When crude CRL and ABL preparations were dried to the same water content as the crosslinked enzyme crystal formulations (13.3% for CRL and 2.5% for ABL) the activities changed by less than 12%.

We believe this to be the first demonstration that pure lipases can be extremely active in organic solvents in heterogeneous form. In addition, crosslinked CRL crystal formulations exhibit much higher enantioselectivity than the crude CRL preparation, containing contaminants with different selectivity (Table, entrees 1–3). In this case, the increased enantioselectivity of the crosslinked enzyme crystal formulation was due to the removal of competing hydrolases [Lalonde et al., supra].

The comparison of crosslinked enzyme crystal formulations with organic soluble lipase complexes is instructive. The specific activity of the LPS-crosslinked enzyme crystal in the resolution of phenethyl alcohol (19.5 μmol/min×mg) and sulcatol (1.48 μmol/min×mg) is either similar to or higher than the activities achieved by soluble complexes in the same reactions [G. Ottolina et al., *Biotechnol. Lett.*, 14, pp. 947–52 (1992) and Okahata et al. (1995), supra]. However, the solubility of these complexes is limited in many organic solvents, thus making the high overall reaction rates difficult to achieve. Crosslinked enzyme crystal formulations according to this invention, on the other hand, can be employed in much higher quantities and, being insoluble, allow for easy separation and recycling.

We believe that surfactants play a critical role in the observed activity enhancement which characterizes the crosslinked enzyme crystal formulations of this invention. See Example 9, infra.

A combination of effects may account for the dramatic increase in activity of pure lipases in crosslinked enzyme crystal form. For example, the presence of amphiphilic surfactants may help to maintain a better water balance and native conformation of amphiphilic lipases, which in crude preparations can in part be achieved by different contaminants such as lipids, celite and other proteins. Finally, surfactants may simply facilitate the transfer of hydrophobic substrate molecules through the layer of tightly bound water to the binding site of an enzyme. While more work is necessary to elucidate the exact mechanism of the effects of surfactants on the crosslinked enzyme crystal formulation activity, the practical consequences of this phenomenon are immediately clear: high specific activity, purity and stability of crosslinked enzyme crystal formulations result in high catalyst productivity in organic solvents.

Example 5

Enzymatic Productivity

In order to demonstrate the productivity of crosslinked enzyme crystal formulations in organic solvents on a preparative scale we chose the resolution of sec-phenethyl alcohol (50 mmol; 6.1 g) with vinyl acetate (50 mmol; 4.3 g) in toluene (100 mL) catalyzed by LPS-crosslinked enzyme crystals (1.3 mg solid; 1 mg protein). The reaction mixture was allowed to stir at room temperature for 16 hours, at which time the conversion reached 50%. The isolated yield of phenethyl acetate was 4.5 g (98.5% ee) giving the volumetric productivity of 30 g/l and substrate to catalyst ratio of 4600. The productivity reached 8000 after 72 hours when 100 mmol sec-phenethyl alcohol was used.

The high productivity of low molecular weight synthetic catalysts is thought to be their key advantage over high molecular weight enzymes [E. N. Jacobsen and N. S. Finney, *Chemistry & Biology*, 1, pp. 85–90 (1994)]. This example clearly demonstrates that despite their high molecular weight and quite-unusual-for-enzymes reaction medium, crosslinked enzyme crystal formulations are highly productive catalysts which compare favorably even with the best of synthetic catalysts.

Example 6

Screening for Surfactants for LPS

Samples of crosslinked LPS crystals were prepared as in Example 1. Each sample was exposed to a different surfactant and then dried in the presence of the organic solvent used in Example 1. Drying was carried out in a 1 ml volume of surfactant and organic solvent. In addition, crosslinked LPS crystals were prepared as in Example 1, and dried as above, without exposure to a surfactant. Enzymatic activity was measured in the resolution of phenylethyl alcohol.

More specifically, 200 mM sec-phenethyl alcohol and 200 mM vinyl acetate in 1 ml toluene were added to 1.2 mg samples of dry crosslinked LPS crystals, some of which had been exposed to surfactants and some of which had not been exposed to surfactants. 10 The reaction was allowed to proceed for 30 minutes, after which the % conversion was measured by gas chromatography. The results are shown in Table 2 below.

TABLE 2

| Surfactant | | % Conversion in 30 Minutes |
|---|---|---|
| Anionic Surfactant: | C5 | 0.5 |
| | Erosol 22 | 6 |
| | Alkyl Sodium Sulfate (NIAPROOF) Type-8 | 1 |
| | Alkyl (C9–C13) Sodium Sulfates (TEEPOL HB7) | <2 |
| Cationic Surfactant: | Methyl trioctylammonium chloride (ALIQUATE 336) | 12 |
| | (EDT-20, ' PEG-10 tallow) | 50 |
| Nonionic Surfactant: | Polyoxyethylene Ethers 4 lauryl Ether (BRIJ 30) | 14 |
| | Octyl phenoxy polyethoxyethanol (TRITONS) | |
| | Tx-15 | 16 |
| | Tx-100 | 15 |
| | Tx-114 | 6 |
| | DF-16 | 37 |
| | N-57 | 39 |
| | DF-12 | 15 |
| | CF-10 | 36 |
| | CF-54 | 35 |
| | Polyoxyethylenesorbitan | |

TABLE 2-continued

| Surfactant | | % Conversion in 30 Minutes |
|---|---|---|
| | Monolaurate (TWEEN 20) | 10 |
| | Sorbitan | |
| | Sesquioleate (ALACEL 83) | 50 |
| | Trioleate (SPAN 85) | 10 |
| | Polyglycol Ether (TERGITOL) | |
| | Type NP-4 | 12 |
| | Type NP-9 | 19 |
| | Type TMN-10 | 3.5 |
| | Type 15-S-3 | 50 |
| | No Surfactant | 3 |

Example 7

Screening for Surfactants for ABL

Samples of crosslinked ABL crystals were prepared in Example 3. Each sample was exposed to a different surfactant and then dried in the presence of the same organic solvent used in Example 3. Drying was carried out in a 1 ml volume of surfactant and organic solvent. In addition, crosslinked ABL crystals were prepared as in Example 3, and dried as above, without exposure to a surfactant. Enzymatic activity was measured in the transesterification of N-Ac-PheOMe with n-propanol in isooctane.

More specifically, 1 ml (11 mg) of N-acetyl-L-phenylalanine methyl ester and 20% 1-propanol in 80% isooctane were added to 1 mg samples of dry crosslinked ABL crystals, some of which had been exposed to surfactants and some of which had not been exposed to surfactants. The reaction was allowed to proceed for 30 minutes, after which the it conversion was measured by gas chromatography. The results are shown in Table 3 below.

TABLE 3

| Surfactant | | % Conversion |
|---|---|---|
| Anionic Surfactant: | Aerosol 22 | 30 |
| | dioctyl sulfosuccinate (AOT) | 98 |
| | Alkyl Sodium Sulfate (Niaproof) | |
| | Type-4 | 69 |
| | Type-4 | 51 |
| | Alkyl(C9–C13)Sodium Sulfates (TEEPOL HB7) | 33 |
| Cationic Surfactant | Methyl trioctylammonium chloride (Aliquat 336) | 93 |
| | N,N',N'-polyoxyethylene (10)-N-tallow-1,3-diaminopropane (EDT-20,' PEG-10 tallow) | 83 |
| Nonionic Surfactant: | Polyoxyethylene Ethers: | |
| | 4 lauryl Ether (BRIJ 30) | 93 |
| | 23 lauryl Ether (BRIJ 35) | 91 |
| | Octyl phenoxy polyethoxyethanol (TRITONS): | |
| | Tx-15 | 43 |
| | Tx-100 | 87 |
| | Tx-114 | 89 |
| | Polyoxyethylenesorbitan: | |
| | Monolaurate (TWEEN 20) | 75 |

TABLE 3-continued

| Surfactant | | % Conversion |
|---|---|---|
| | Sorbitan: | |
| | Sesquioleate (ARLACEL 83) | 39 |
| | Trioleate (SPAN 85) | 38 |
| | Polyglycol Ether (TERGITOL): | |
| | Type NP-4 | 89 |
| | Type NP-9 | 88 |
| | Type NP-35 | 95 |
| | Type TMN-6 (2,6,8, Trimethyl-4-nonyloxypoly-ethylenoxyethanol | 85 |
| | Type TMN-10 | 91 |
| | Type 15-S-3 | 95 |
| | Type 15-S-40 | 88 |
| | No Surfactant | 26 |

Example 8

Screening for Surfactants for CRL

Samples of crosslinked CRL crystals were prepared as in Example 2. Each sample was exposed to a different surfactant and then dried in the presence of the same organic solvent used in Example 2. Drying was carried out in a 1 ml volume of surfactant and organic solvent. In addition, crosslinked CRL crystals were prepared as in Example 2, and dried as above, without exposure to a surfactant. Enzymatic activity was measured in the transesterification of N-amyl alcohol with ethyl acetate in toluene.

More specifically, 184 nM n-amyl alcohol in ethyl acetate and 1 ml toluene was added to 2 mg samples of dry crosslinked CRL crystals, some of which had been exposed to surfactants and some of which had not been exposed to surfactants. The reaction was allowed to proceed for 30 minutes, after which the % conversion was measured by gas chromatography. The results are shown in Table 4 below.

TABLE 4

| Surfactant | | % Conversion |
|---|---|---|
| Anionic Surfactant: | Aerosol 22 | 12 |
| | dioctyl sulfosuccinate (AOT) | 13 |
| | TRITON QS-30 | 13 |
| Cationic Surfactant | EDT-20, PEG-10 tallow | 9 |
| Nonionic Surfactant | Octyl phenoxy polyethoxyethanol | |
| | TX-15 | 16 |
| | TX-114 | 17 |
| | DF-16 | 9 |
| | N-57 | 9 |
| | NP-4 | 11 |
| | Polyoxyethylenesorbitan: | |
| | Monolaurate (TWEEN 20) | 11 |
| | Sorbitan: | |
| | Sesquioleate (ARLACEL 83) | 15 |
| | Polyglycol Ether (TERGITOL) | |
| | Type TMN-6 | 16 |
| | Type 15-S-3 | 12 |
| | Type 15-S-40 | 10 |
| | No surfactant | 0 |

Example 9

Effect of Surfactants

The following example demonstrates the critical role of surfactants in the activity enhancement displayed by crosslinked enzyme crystal formulations according to this invention. We prepared crosslinked enzyme crystals as described in Examples 1–3, except that we dried them to a water content similar to that of the crosslinked enzyme crystal formulations of those examples, without the use of surfactants. Those water content levels were—13.3% water content for CRL; 1.7–2% water content for LPS and 2.2–2.4% water content for ABL.

For each enzyme sample, drying was carried out in the presence of the same solvent used for that particular enzyme in Example 1, 2 or 3, on a smaller (1 ml) scale. We then measured initial activity levels, rather than % conversion, in the assays described in Examples 6–8 for the respective enzyme. We also measured the initial activity of each of the crosslinked enzyme crystal formulations of Examples 1–3 in the respective assay for that enzyme (CRL assay: Example 8; LPS assay: Example 6; ABL assay: Example 7). As compared with the initial activity levels of the crosslinked enzyme crystal formulations of Examples 1–3, the initial activity of the crosslinked enzyme crystals dried without surfactants were 19-fold (ABL), 79-fold (LPS) and more than 100-fold lower (CRL).

TABLE 5

| Enzyme | % moisture | initial activity ($\mu$mol/min × mg) | enzyme (mg/ml) |
|---|---|---|---|
| CRL dry no surfactant | 13.5 | 0.0 | 3.5 |
| CRL dry surfactant | 13.2 | 0.25 | 2.0 |
| LPS dry no surfactant | 2.3 | 0.09 | 5.3 |
| LPS dry surfactant | 2.0 | 7.1 | 0.1 |
| ABL dry no surfactant | 2.4 | 0.03 | 6.6 |
| ABL dry surfactant | 2.2 | 0.58 | 0.3 |

% of surfactant in the crosslinked enzyme crystal formulations:

| Enzyme | % Surfactant |
|---|---|
| CRL | 25–30 |
| LPS | 40–45 |
| ABL | 40–45 |

Example 10

Screening of Surfactants

We used an alternate procedure to screen a number of anionic, cationic and nonionic surfactants for use in producing crosslinked enzyme crystal formulations according to this invention. In this screening procedure, enzyme activity of crosslinked enzyme crystal formulations prepared as in Examples 6–8 was measured after drying crosslinked enzyme crystals in a given surfactant in the presence of an organic solvent and after 12 days storage at room temperature. Activity of dry samples of CRL was measured in the transesterification of n-amyl alcohol with ethyl acetate in toluene, as described in Example 8. Activity of dry samples of ABL was measured in transesterification of N-Ac-PheOMe with n-propanol in isooctane, as described in Example 7. Activity of dry samples of LPS was measured in the resolution of phenylethyl alcohol, as described in Example 6. While enzymes exposed to several of the surfactants exhibited high activity after drying, only a few maintained this high level after storage. In addition to the surfactants used in these examples, several others—Tritons and dioctyl sulfosuccinate for CRL and dioctyl sulfosuccinate and 4 lauryl ether for ABL—provided crosslinked enzyme crystal formulations that exhibited high activity after storage.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

I claim:

1. A method for using a crosslinked enzyme crystal formulation to produce a selected product in an organic solvent or an aqueous-organic solvent mixture, said method comprising the steps of:

(a) combining at least one substrate and at least one crosslinked enzyme crystal formulation which acts upon said substrate in the presence of an organic solvent or an aqueous-organic solvent mixture, said crosslinked enzyme crystal formulation comprising crosslinked enzyme crystals and a surfactant, said crosslinked enzyme crystal formulation being characterized by an enzyme activity in an organic solvent or an aqueous-organic solvent mixture which is at least about 1.7 times greater than the enzyme activity of the equivalent amount of said enzyme in either crude form or pure form; and (b) maintaining the combination produced in step (a) under conditions which permit said enzyme to act upon the substrate, thereby producing said product in said organic solvent or aqueous-organic solvent mixture.

2. A method for using a crosslinked enzyme crystal formulation to produce a selected product in an organic solvent or an aqueous-organic solvent mixture, said method comprising the steps of:

(a) combining at least one substrate and at least one crosslinked enzyme crystal formulation which acts upon said substrate in the presence of an organic solvent or an aqueous-organic solvent mixture, said crosslinked enzyme crystal formulation comprising crosslinked enzyme crystals and a surfactant, said crosslinked enzyme crystal formulation being characterized by having at least about 4.3 times greater specific activity per milligram of solid in an organic solvent or an aqueous-organic solvent mixture than that of said enzyme in either crude form or pure form; and (b) maintaining the combination produced in step (a) under conditions which permit said enzyme to act upon the substrate, thereby producing said product in said organic solvent or aqueous-organic solvent mixture.

3. A method for using a crosslinked enzyme crystal formulation to produce a selected product in an organic solvent or an aqueous-organic sol-vent mixture, said method comprising the steps of:

(a) combining at least one substrate and at least one crosslinked enzyme crystal formulation which acts upon said substrate in the presence of an organic solvent or an aqueous-organic solvent mixture, said crosslinked enzyme crystal formulation comprising crosslinked enzyme crystals and a surfactant, said crosslinked enzyme crystal formulation being characterized by having at least about 19 times greater enzyme activity in an organic solvent or an aqueous-organic solvent mixture than the activity of crosslinked crystals of said enzyme containing no surfactant; and (b) maintaining the combination produced in step (a) under conditions which permit said enzyme to act upon the substrate, thereby producing said product in said organic solvent or aqueous-organic solvent mixture.

4. The method according to any one of claims 1, 2 or 3, wherein said product is selected from the group consisting of chiral organic molecules, peptides, carbohydrates and lipids.

5. The method according to claim 1, wherein said enzyme is selected from the group consisting of hydrolases, isomerases, lyases, ligases, transferases and oxidoreductases.

6. The method according to claim 5, wherein said enzyme is a hydrolase.

7. The method according to claim 6, wherein said hydrolase is selected from the group consisting of thermolysin, elastase, esterase, lipase, nitrilase, hydantoinase, protease, asparaginase, urease and lysozyme.

8. The method according to any one of claims 1, 2 or 3, wherein said organic solvent is selected from the group consisting of octanes, diols, polyols, polyethers and water soluble polymers.

9. The method according to claim 8, wherein said organic solvent is selected from the group consisting of toluene, octane, tetrahydrofuran, acetone, pyridine, diethylene glycol, 2-methyl-2,4-pentanediol, poly(ethylene glycol), triethylene glycol, 1,4-butanediol, 1,2-butanediol, 2,3,-dimethyl-2,3-butanediol, 1,2-butanediol, dimethyl tartrate, monoalkyl ethers of poly(ethylene glycol), dialkyl ethers of poly(ethylene glycol), and polyvinylpyrrolidone.

* * * * *

UNITED STATES PATENT AND TRADEMARK OFFICE
CERTIFICATE OF CORRECTION

PATENT NO. : 6,042,824
DATED : March 28, 2000
INVENTOR(S) : Nazer K. Khalaf

It is certified that error appears in the above-identified patent and that said Letters Patent is hereby corrected as shown below:

Title page,
Item [54], change "CROSS LINKED" to -- CROSSLINKED --;

Column 1,
Line 1, title, change "CROSS LINKED" to -- CROSSLINKED --;
Line 42, change "transformations" to -- Transformations --;
Line 44, change "(1990]." to -- (1990). --;

Column 2,
Line 3, change "Biol," to -- Biol. --;

Column 3,
Line 57, change "ou" to -- or --;

Column 5,
Line 26, change "Industrial" to -- industrial --;

Column 7,
Line 24, change "wish" to -- with --;

Column 11,
Line 17, insert -- ) -- after "nonyloxypolyethylenoxyethanol";
Line 33, change "co" to -- of --;

Column 13,
Line 26, change "Ca $(Cl_3COO)^{2}$" to -- Ca $(Cl_3COO)_2$ --;

Column 14,
Line 7, delete "X";

Column 15,
Line 3, change "tc" to -- to --;
Line 39, change "Gradient," to -- $Gradient_2$ --;

Column 16,
Line 21, change "rate 5°" to -- rate=5° --;
Line 35, change "Cailf .)" to -- Calif .) --;
Line 43, change "98.53" to -- 98.5% --;
Line 46, change "6815" to -- 6845 --;
Line 66, change "66.1%,." to -- 66.1%. --;

UNITED STATES PATENT AND TRADEMARK OFFICE
CERTIFICATE OF CORRECTION

PATENT NO. : 6,042,824
DATED : March 28, 2000
INVENTOR(S) : Nazer K. Khalaf

It is certified that error appears in the above-identified patent and that said Letters Patent is hereby corrected as shown below:

Column 17,
Line 65, change "ee>98," to -- 33>98% --;

Column 20,
Line 37, delete "10";
Line 45, change "C5" to -- TRITON QS-30 (octyl phenoxy polyethoxyethanol) --;
Line 47, change "Erosol" to -- AEROSOL --;

Column 21,
Line 8, change "(ALACEL" to -- (ARLACEL --;
Line 38, change "it" to -- % --;

Column 24,
Line 1, change "Tritons" to -- TRITONS --;
Line 56, change "sol-vent" to -- solvent --;

Column 25,
Line 10, change "to claim 1," to -- to any one of claims 1, 2 or 3, --.

Signed and Sealed this

Sixth Day of November, 2001

*Attest:*

NICHOLAS P. GODICI
*Attesting Officer*    Acting Director of the United States Patent and Trademark Office